US007805199B2

United States Patent
KenKnight et al.

(10) Patent No.: US 7,805,199 B2
(45) Date of Patent: *Sep. 28, 2010

(54) METHOD AND APPARATUS FOR ESTABLISHING CONTEXT AMONG EVENTS AND OPTIMIZING IMPLANTED MEDICAL DEVICE PERFORMANCE

(75) Inventors: Bruce H. KenKnight, Maple Grove, MN (US); Eric G. Lovett, Roseville, MN (US); Robert J. Sweeney, Woodbury, MN (US); Scott T. Mazar, Inver Grove Heights, MN (US); Yatheendhar Manicka, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 213 days.

This patent is subject to a terminal disclaimer.

(21) Appl. No.: 11/381,051

(22) Filed: May 1, 2006

(65) Prior Publication Data

US 2006/0195163 A1   Aug. 31, 2006

Related U.S. Application Data

(63) Continuation of application No. 10/093,353, filed on Mar. 6, 2002, now Pat. No. 7,043,305.

(51) Int. Cl.
*A61N 1/08* (2006.01)
(52) U.S. Cl. .......................................... 607/60; 607/32
(58) Field of Classification Search ................ 600/300, 600/510, 523; 607/5, 9, 30, 32, 46, 59, 60
See application file for complete search history.

(56) References Cited

U.S. PATENT DOCUMENTS

| | | | |
|---|---|---|---|
| 4,712,179 | A | 12/1987 | Heimer |
| 4,777,960 | A | 10/1988 | Berger et al. |
| 4,796,634 | A | 1/1989 | Huntsman et al. |
| 4,809,697 | A | 3/1989 | Causey, III et al. |

(Continued)

FOREIGN PATENT DOCUMENTS

EP   0297675 A1   1/1989

(Continued)

OTHER PUBLICATIONS

"International Search Report for corresponding PCT Application No. PCT/US 03/06851", (Nov. 25, 2004),4 Pages.

(Continued)

*Primary Examiner*—Carl H Layno
*Assistant Examiner*—Luther G Behringer
(74) *Attorney, Agent, or Firm*—Schwegman, Lundberg & Woessner, P.A.

(57) ABSTRACT

An apparatus and method for adjusting the performance of an implanted device based on data including contextual information. Contextual information, including operational and performance data concerning the implanted device as well as the patient with the implanted device, is stored by a portable electronic device. In one embodiment, the portable electronic device is adapted for battery operation and includes a personal digital assistant (PDA). The portable electronic device is adapted for use as an interface to conduct wireless communications with the implanted device. In one embodiment, the portable electronic device interfaces with a clinical programmer for use by a physician.

24 Claims, 12 Drawing Sheets

U.S. PATENT DOCUMENTS

| | | | |
|---|---|---|---|
| 4,825,869 A | 5/1989 | Sasmor et al. | |
| 4,838,275 A | 6/1989 | Lee | |
| 4,928,688 A | 5/1990 | Mower | |
| 5,047,930 A | 9/1991 | Martens et al. | |
| 5,097,831 A | 3/1992 | Lekholm | |
| 5,113,869 A | 5/1992 | Nappholz et al. | |
| 5,174,289 A | 12/1992 | Cohen | |
| 5,226,413 A | 7/1993 | Bennett et al. | |
| 5,251,626 A | 10/1993 | Nickolls et al. | |
| 5,262,944 A | 11/1993 | Weisner et al. | |
| 5,282,838 A | 2/1994 | Hauser et al. | |
| 5,292,341 A | 3/1994 | Snell | |
| 5,309,919 A | 5/1994 | Snell et al. | |
| 5,311,873 A | 5/1994 | Savard et al. | |
| 5,321,618 A | 6/1994 | Gessman | |
| 5,372,607 A | 12/1994 | Stone et al. | |
| 5,421,830 A | 6/1995 | Epstein et al. | |
| 5,540,727 A | 7/1996 | Tockman et al. | |
| 5,549,654 A | 8/1996 | Powell | |
| 5,594,638 A | 1/1997 | Iliff | |
| 5,607,460 A | 3/1997 | Kroll et al. | |
| 5,613,495 A | 3/1997 | Mills et al. | |
| 5,626,630 A | 5/1997 | Markowitz et al. | |
| 5,630,835 A | 5/1997 | Brownlee | |
| 5,690,690 A | 11/1997 | Nappholz et al. | |
| 5,693,076 A | 12/1997 | Kaemmerer | |
| 5,716,382 A | 2/1998 | Snell | |
| 5,720,771 A | 2/1998 | Snell | |
| 5,722,999 A | 3/1998 | Snell | |
| 5,724,985 A | 3/1998 | Snell et al. | |
| 5,759,199 A | 6/1998 | Snell et al. | |
| 5,792,064 A | 8/1998 | Panescu et al. | |
| 5,800,473 A | 9/1998 | Faisandier | |
| 5,833,623 A | 11/1998 | Mann et al. | |
| 5,860,918 A | 1/1999 | Schradi et al. | |
| 5,891,178 A | 4/1999 | Mann et al. | |
| 5,911,132 A | 6/1999 | Sloane | |
| 5,935,081 A | 8/1999 | Kadhiresan | |
| 6,001,060 A | 12/1999 | Churchill et al. | |
| 6,016,442 A | 1/2000 | Hsu et al. | |
| 6,024,089 A | 2/2000 | Wallace et al. | |
| 6,070,101 A | 5/2000 | Struble et al. | |
| 6,091,990 A | 7/2000 | Hsu et al. | |
| 6,093,146 A | 7/2000 | Filangeri | |
| 6,102,874 A | 8/2000 | Stone et al. | |
| 6,115,630 A | 9/2000 | Stadler et al. | |
| 6,168,563 B1 | 1/2001 | Brown | |
| 6,190,324 B1 | 2/2001 | Kieval et al. | |
| 6,240,317 B1 | 5/2001 | Villaseca et al. | |
| 6,249,703 B1* | 6/2001 | Stanton et al. | 607/30 |
| 6,250,309 B1 | 6/2001 | Krichen et al. | |
| 6,263,245 B1 | 7/2001 | Snell et al. | |
| 6,275,727 B1 | 8/2001 | Hopper et al. | |
| 6,280,409 B1 | 8/2001 | Stone et al. | |
| 6,304,773 B1 | 10/2001 | Taylor et al. | |
| 6,331,160 B1* | 12/2001 | Bardy | 600/300 |
| 6,336,900 B1 | 1/2002 | Alleckson et al. | |
| 6,336,903 B1 | 1/2002 | Bardy | |
| 6,351,675 B1 | 2/2002 | Tholen et al. | |
| 6,363,282 B1 | 3/2002 | Nichols et al. | |
| 6,368,284 B1 | 4/2002 | Bardy | |
| 6,381,496 B1* | 4/2002 | Meadows et al. | 607/59 |
| 6,383,136 B1 | 5/2002 | Jordan | |
| 6,398,728 B1 | 6/2002 | Bardy | |
| 6,411,840 B1 | 6/2002 | Bardy | |
| 6,411,847 B1 | 6/2002 | Mower | |
| 6,438,407 B1 | 8/2002 | Ousdigian et al. | |
| 6,438,408 B1 | 8/2002 | Mulligan et al. | |
| 6,440,066 B1 | 8/2002 | Bardy | |
| 6,442,433 B1 | 8/2002 | Linberg | |
| 6,443,890 B1 | 9/2002 | Schulze et al. | |
| 6,453,201 B1 | 9/2002 | Daum et al. | |
| 6,480,745 B2 | 11/2002 | Nelson et al. | |
| 6,497,655 B1 | 12/2002 | Linberg et al. | |
| 6,514,195 B1 | 2/2003 | Ferek | |
| RE38,119 E | 5/2003 | Mower | |
| 6,564,104 B2 | 5/2003 | Nelson et al. | |
| 6,564,105 B2 | 5/2003 | Starkweather et al. | |
| 6,579,231 B1 | 6/2003 | Phipps | |
| 6,585,644 B2 | 7/2003 | Lebel et al. | |
| 6,592,528 B2 | 7/2003 | Amano | |
| 6,622,045 B2 | 9/2003 | Snell et al. | |
| 6,628,989 B1 | 9/2003 | Penner et al. | |
| 6,648,823 B2 | 11/2003 | Thompson et al. | |
| 6,650,939 B2 | 11/2003 | Taepke, II et al. | |
| 6,650,944 B2 | 11/2003 | Goedeke et al. | |
| 6,669,631 B2 | 12/2003 | Norris et al. | |
| 6,684,103 B2 | 1/2004 | Ding et al. | |
| 6,687,547 B2 | 2/2004 | Goedeke et al. | |
| 6,738,667 B2 | 5/2004 | Deno et al. | |
| 6,764,446 B2 | 7/2004 | Wolinsky et al. | |
| 6,804,558 B2 | 10/2004 | Haller et al. | |
| 6,931,273 B2 | 8/2005 | Groenewegen et al. | |
| 6,944,495 B2 | 9/2005 | MacAdam et al. | |
| 6,975,900 B2 | 12/2005 | Rudy et al. | |
| 7,024,248 B2 | 4/2006 | Penner et al. | |
| 7,043,305 B2* | 5/2006 | KenKnight et al. | 607/60 |
| 7,123,953 B2 | 10/2006 | Starobin et al. | |
| 7,203,549 B2* | 4/2007 | Schommer et al. | 607/60 |
| 7,273,457 B2 | 9/2007 | Penner | |
| RE39,897 E | 10/2007 | Mower | |
| 7,468,032 B2 | 12/2008 | Stahmann et al. | |
| 2001/0007053 A1 | 7/2001 | Bardy | |
| 2001/0012955 A1 | 8/2001 | Goedeke et al. | |
| 2001/0031997 A1 | 10/2001 | Lee | |
| 2001/0039375 A1 | 11/2001 | Lee et al. | |
| 2001/0047125 A1 | 11/2001 | Quy | |
| 2001/0049544 A1 | 12/2001 | Lee | |
| 2001/0051787 A1 | 12/2001 | Haller et al. | |
| 2002/0013613 A1* | 1/2002 | Haller et al. | 607/60 |
| 2002/0013614 A1 | 1/2002 | Thompson | |
| 2002/0016550 A1 | 2/2002 | Sweeney et al. | |
| 2002/0019586 A1 | 2/2002 | Teller et al. | |
| 2002/0023654 A1 | 2/2002 | Webb | |
| 2002/0026103 A1 | 2/2002 | Norris et al. | |
| 2002/0026223 A1 | 2/2002 | Riff et al. | |
| 2002/0049482 A1 | 4/2002 | Fabian et al. | |
| 2002/0052539 A1 | 5/2002 | Haller et al. | |
| 2002/0077562 A1* | 6/2002 | Kalgren et al. | 600/510 |
| 2002/0082868 A1 | 6/2002 | Pories et al. | |
| 2002/0120311 A1 | 8/2002 | Lindh et al. | |
| 2002/0123672 A1 | 9/2002 | Christophersom et al. | |
| 2002/0173830 A1* | 11/2002 | Starkweather et al. | 607/60 |
| 2003/0055406 A1* | 3/2003 | Lebel et al. | 604/891.1 |
| 2003/0055679 A1 | 3/2003 | Soll et al. | |
| 2003/0088290 A1 | 5/2003 | Spinelli et al. | |
| 2003/0093127 A1* | 5/2003 | Dalal | 607/32 |
| 2003/0144711 A1* | 7/2003 | Pless et al. | 607/60 |
| 2003/0171791 A1 | 9/2003 | KenKnight et al. | |
| 2003/0235816 A1 | 12/2003 | Slawin et al. | |
| 2004/0019287 A1 | 1/2004 | White | |
| 2004/0117204 A1 | 6/2004 | Mazar et al. | |
| 2004/0122294 A1 | 6/2004 | Hatlestad et al. | |
| 2004/0122295 A1 | 6/2004 | Hatlestad et al. | |
| 2004/0122296 A1 | 6/2004 | Hatlestad et al. | |
| 2004/0122297 A1 | 6/2004 | Stahmann et al. | |
| 2004/0122484 A1 | 6/2004 | Hatlestad et al. | |
| 2004/0122485 A1 | 6/2004 | Stahmann et al. | |
| 2004/0122486 A1 | 6/2004 | Stahmann et al. | |
| 2004/0122487 A1 | 6/2004 | Hatlestad et al. | |

FOREIGN PATENT DOCUMENTS

| | | |
|---|---|---|
| EP | 0362611 A1 | 4/1990 |

| | | |
|---|---|---|
| EP | 0709058 A1 | 5/1996 |
| WO | WO-00/41765 A1 | 7/2000 |
| WO | WO-00/41766 A1 | 7/2000 |
| WO | WO-01/03575 A1 | 1/2001 |
| WO | WO-01/24876 A1 | 4/2001 |
| WO | WO 031075744 * | 9/2003 |

OTHER PUBLICATIONS

Barbaro, V., et al., "A Portable Unit for Remote Monitoring of Pacemaker Patients", *Journal of Telemedicine and Telecare*, 3(2), (1997), 96-102.

Bourge, R., et al., "Noninvasive Rejection Monitoring of Cardiac Transplants Using High Resolution Intramyocardial Electrograms", *PACE*, vol. 21, Part II, (Nov. 1998), 2338-2344.

Girouard, S. D., et al., "Cardiac Rhythm Management Systems and Methods Predicting Congestive Heart Failure Status", Application Filed: Aug. 6, 2002 U.S. Appl. No. 10/213,268, 33 pgs.

Hatlestad, J., "Methods and Devices for Detection of Context When Addressing a Medical Condition of a Patient", Application Filed: Oct. 11, 2002 U.S. Appl. No. 10/269,611, CPI Reference No. 01-173, 29 pgs.

Hutten, H., et al., "Cardiac Pacemaker as Bridge to Cardiac Telemonitoring", *Biomedizinische Technik*, 41(6), *Institut for Elektro-und Biomedizinische Technik Technische Universitat Graz.*, [Article in German With English Abstract], (Jun. 1996),158-165.

Hutten, H., et al., "Cardiac Telemonitoring through the Linkage of Close-up Telemetry and Internet Transmission", *Institute for Electro- and Biomedical Technology, Technical University of Graz Inffeldgasse*, 42, [Article in German with English Abstract],(1997), 67-69.

Ji, J., "An Ultraminiature CMOS Pressure Sensor for a Multiplexed Cardiovascular Catheter", *IEEE Transactions on Electron Devices*, vol. 39, No. 10, (Oct. 1992), 2260-2267.

Mower, M., "Method and Apparatus for Treating Hemodynamic Disfunction", U.S. Patent Office Patent Application Information Retrieval (PAIR) search results for U.S. Appl. No. 10/214,474, filed Aug. 8, 2002, 3 pgs.

Smith, R.A., et al., "An Intranet Database for Pacemaker Patients", *International Journal of Medical Informatics*, 47, (1997), 79-82.

Zhu, Q., et al., "Method and Apparatus for Determining Changes in Heart Failure Status", Application Filed: Nov. 15, 2001 U.S. appl. No. 10/001,223, 22 pgs.

"European Application Serial No. 03713931 (Atty Ref 279.364EP1), Office Action mailed Jul. 22, 2008", 4 pgs.

"U.S. Appl. No. 10/323,604, Non-Final Office Action mailed Apr. 21, 2009", 20 pgs.

"U.S. Appl. No. 10/323,604, Response filed Feb. 19, 2009 to Final Office Action mailed Aug. 19, 2008", 14 pgs.

"U.S. Appl. No. 10/323,604, Final Office Action mailed Aug. 19, 2008", 16 pgs.

"U.S. Appl. No. 10/323,606, Examiner's Answer mailed Feb. 26, 2008", 29 pgs.

"U.S. Appl. No. 10/323,606, Reply Brief mailed Apr. 28, 2008", 9 pgs.

"U.S. Appl. No. 10/323,607, Response filed Jun. 22, 2005 to Final Office Action mailed Mar. 23, 2005", 12 pgs.

"U.S. Appl. No. 10/323,607, Non-Final Office Action mailed Oct. 22, 2008", 6 pgs.

"U.S. Appl. No. 10/323,607, Response filed Sep. 13, 2005 to Notice of Non-Compliant Amendment mailed Sep. 8, 2005", 12 pgs.

"U.S. Appl. No. 10/323,607, Response filed Feb. 23, 2009 to Non Final Office Action mailed Oct. 22, 2008", 9 pgs.

"U.S. Appl. No. 10/323,607, Supplemental Amendment and Response filed May 22, 2007 to Final Office Action mailed Aug. 1, 2006", 10 pgs.

"U.S. Appl. No. 10/323,607, Non-Final Office Action mailed Aug. 24, 2009", 9 pgs.

"U.S. Appl. No. 10/323,616, Final Office Action mailed on Nov. 13, 2009", 19 pgs.

"U.S. Appl. No. 10/323,616, Non-Final Office Action mailed Apr. 2, 2009", 22 pgs.

"U.S. Appl. No. 10/323,616, Response filed Aug. 3, 2009 to Non Final Office Action mailed Apr. 2, 2009", 19 pgs.

"U.S. Appl. No. 10/323,616, Response filed Mar. 13, 2009 to Final Office Action mailed Nov. 13, 2009", 17 pages.

"U.S. Appl. No. 10/323,713, Preliminary Amendment mailed Dec. 17, 2003", 14 pgs.

"U.S. Appl. No. 10/323,859, Non-Final Office Action mailed Oct. 17, 2008", 7 pgs.

"U.S. Appl. No. 10/323,859, Final Office Action mailed Jul. 9, 2009", 9 Pgs.

"U.S. Appl. No. 10/323,859, Response filed Mar. 17, 2009 to Non-Final Office Action mailed Oct. 17, 2008", 20 pages.

"U.S. Appl. No. 10/323,860, Response filed Nov. 24, 2008 to Non Final Office Action mailed Jul. 22, 2008", 17 pgs.

"U.S. Appl. No. 10/323,860, Final Office Action mailed Mar. 5, 2009", 13 pgs.

"U.S Appl. No. 10/323,860, Response filed Aug. 31, 2009 to Advisory Action mailed Aug. 19, 2009", 16 pgs.

"U.S. Appl. No. 10/323,860, Response filed Aug. 4, 2009 to Final Office Action mailed Mar. 5, 2009", 14 pgs.

03713931.8, "European Application Serial No. 03713931.8, Office Action mailed May 20, 2009", 2 pgs.

"European Application Serial No. 03713931.8, Response filed Jan. 15, 2009 to Communication dated Jul. 22, 2008", 17 pgs.

"European Application Serial No. 03713931.8, Response filed Sep. 18, 2009 to Communication dated May 20, 2009", 4 pgs.

* cited by examiner

Fig.1B 465
- ARE YOU CURRENTLY EXCERCISING?
- HAVE YOU TAKEN YOUR PRESCRIBED MEDICINE?
- HAVE YOU TAKEN ANY NON-PRESCRIPTION DRUGS?
- HAVE YOU CONSUMED ALCOHOL?
- DID YOU SLEEP LESS THAN 6 HOURS LAST NIGHT?

Fig.1C 470
- ARE YOU FEELING ALERT?
- ARE YOU EXPERIENCING ANY UNUSUAL SENSATIONS?
- DO YOU HAVE ANY CHEST PAIN?
- ARE YOU ANXIOUS FOR ANY REASON?
- ARE YOU UNDER STRESS?

Fig.1D 475
- ARE YOU EATING A BALANCED DIET?
- ARE YOU LETHARGIC?
- ARE YOU EXPERIENCING INSOMNIA?
- ARE YOUR VOIDING PATTERNS ROUTINE?
- HAVE YOU TAKEN ANY NARCOTICS?

Fig.1E 480
- ARE YOU PLANNING EXERCISING IN THE NEXT 3 HOURS?
- HOW MANY ALCOHOLIC DRINKS HAVE YOU CONSUMED IN THE PREVIOUS 2 HOURS?
- ARE YOU ABOVE YOUR TARGET BODY WEIGHT?
- ARE YOUR LEGS OR ANKLES SWOLLEN?
- ARE YOU HAVING DIFFICULTY BREATHING?

METHOD AND APPARATUS FOR ESTABLISHING CONTEXT AMONG EVENTS AND OPTIMIZING IMPLANTED MEDICAL DEVICE PERFORMANCE

RELATED APPLICATIONS

This application is a Continuation of U.S. application Ser. No. 10/093,353, now U.S. Pat. No. 7,043,305 filed on Mar. 6, 2002, which is incorporated herein by reference.

TECHNICAL FIELD

The present subject matter relates to implantable devices and more specifically, to a method and system for optimizing performance of an implanted medical device based on contextual information derived from the implanted medical device, external sensors, user provided data, or other sources.

BACKGROUND

A normal, healthy, heart beats at a regular rate. Irregular heart beats, known as cardiac arrhythmia, on the other hand, may characterize an unhealthy condition. Another unhealthy condition is known as congestive heart failure ("CHF"). CHF, also known as heart failure, is a condition where the heart has inadequate capacity to pump sufficient blood to meet metabolic demand. CHF may be caused by a variety of sources, including, coronary artery disease, myocardial infarction, high blood pressure, heart valve disease, cardiomyopathy, congenital heart disease, endocarditis, myocarditis, and others.

Unhealthy heart conditions may be treated using a cardiac rhythm management (CRM) system. Examples of CRM systems, or pulse generator systems, include defibrillators (including implantable cardioverter defibrillator), pacemakers and other cardiac resynchronization devices.

Typically, a pulse generator is surgically implanted under the skin, but outside the thorax of a patient and includes one or more conductive lead wires that deliver an electrical pulse to the heart according to a therapy schedule. The electrical pulses may be delivered on a predetermined schedule, on an as needed basis, or according to other predetermined criteria.

In some cases, the operation of the pulse generator may be adjusted using an external programmer. The programmer allows a physician to tailor the performance of the pulse generator without performing surgery on the patient. The programmer may communicate with the pulse generator by wireless technology such as radio frequency communication.

A typical programmer includes a wand coupled to a desktop unit by a flexible electrical cord. In use, the operator positions the wand near the implanted device and a signal from the programmer is wirelessly transmitted to the device. Data is extracted from the transmitted signal and stored in internal memory within the implanted device. The implanted device then delivers therapy according to the memory contents. The memory contents may include operating parameters or programming. For example, the implanted device may be wirelessly programmed to deliver electrical shocks at a greater amplitude or with greater frequency.

The ability to wirelessly program an implantable device has taxed the performance and capacity of device data storage and the device power supply and also compelled the addition of a transceiver suitable for communicating with the programmer. To address these needs, some manufacturers have adapted their devices to include additional circuitry as well as increased battery capacity. To the chagrin of the patient, such improvements have, in some instances, resulted in larger case sizes for the implantable device.

Consumer, and therefore, manufacturers, of implanted medical devices have demonstrated a clear desire for, among other things, reduced device size, increased functionality, and increased reliability and longevity. Efforts to provide increased functionality and increased reliability have tended to frustrate the objective of reduced device size. Thus, there is a need for an implanted device with reduced size and yet permits field programmability along with increased reliability.

At initial implantation, the medical device is programmed to provide therapy based on known parameters and conditions of the patient. Follow-up programming of the implanted device, which may take place at a doctor's office, may be based on stored data and patient input. However, for many patients, follow-up visits are infrequent and thus, patients are unable to provide their physician with accurate or complete information regarding the events surrounding a particular cardiac event. For example, few patients are able to provide reliable data concerning their dietary intake just prior to a period of increased heart rate that may have occurred three weeks ago. Thus, there is a need for collecting timely patient data with improved accuracy.

SUMMARY

The present subject matter includes, among other things, a system and method for collecting timely data from a variety of sources and correlating the data with data provided by an implanted medical device. In one embodiment, patient responses are collected using a portable device. The portable device may present questions or data entry prompts or otherwise solicit a response from the patient. The prompts may concern subjective or objective data. In one embodiment, the questions include "Have you felt dizzy in the last two hours?," "Are you breathless?," "Do you feel palpitations?," "Do you have any chest pain?," and "How many alcoholic drinks have you consumed in the previous 2 hours?" In one embodiment, data from a sensor coupled to the implanted medical device is communicated to the portable device. The data includes physiological information concerning the performance of the implanted medical device or measured parameters concerning a particular body organ or system. In one embodiment, data from a sensor not coupled to the implanted medical device is communicated to the portable device.

By way of example, in one embodiment, the patient is implanted with a medical device as part of a cardiac rhythm management (CRM) system. The CRM system includes a pacemaker defibrillator with an accelerometer and heart rhythm sensor. In addition, the patient is also fitted with an implanted respiration monitor with in the CRM system. In this example, the portable device, which is carried external from the body of the patient, prompts the patient with questions concerning such topics as their sleep patterns, dietary and drug intake, visible edema and other relevant signs and symptoms. The portable device also receives data from the defibrillator with the accelerometer, heart rhythm monitor and the respiration monitor.

At a clinical setting, or by a remote communication coupling, the patient's doctor can access the portable device and retrieve the stored data from the various inputs. The retrieved data can be analyzed for trends as part of a wellness monitoring system and therefore, enable improved medical care and reduce healthcare utilization.

In one embodiment, the portable device is coupled to, or incorporated within a personal digital assistant (PDA). Thus, the PDA communicates wirelessly with an implanted medical device as well as communicates with a programmer. In addition, the portable device is adapted to execute instructions that prompts the user for information and stores the responses. In one embodiment, the user entered data is received in response to a prompt or message. In one embodiment, the user is able to enter data in a free-text entry mode without regard to a particular schedule. In one embodiment, the portable device also receives data from non-invasive sensors or detectors. Examples of non-invasive sensors include an arterial blood pressure monitor, a respiration monitor, a blood sugar detector, a body mass scale as well as other devices. The portable device communicates with the non-invasive sensors or detectors in a wireless manner or via a wired coupling.

In one embodiment, the portable device may receive data from an implanted device other than that which is controllable by way of the programmer. For example, a patient may be equipped with an implanted cardiac pacing device as well as a separate implanted sensor for monitoring a body parameter or organ and the portable device receives data from both implanted devices and yet the programmer interfaces with and controls the operation of the cardiac pacing device and not the separate implanted sensor.

In various embodiments, the portable device is coupled to a PDA, (variously referred to as a personal digital, or data, assistant), a portable telephone (including a cellular telephone or a cordless telephone), a pager (one way or two way), a handheld, palm-top, laptop, portable or notebook computer, or other such battery operated portable communication device, all of which are herein referred to as portable communicators.

In one embodiment, the portable device operates independently and without coupling to a portable communicator. It will be appreciated that either the portable device or the portable communicator may provide the data storage capacity, processing, display, or user input means as described herein.

In one embodiment, the portable device includes circuitry or executable programming and communicates wirelessly with the implanted medical device. In one embodiment, the portable device is coupled by a wired link to a remote programmer or other network communication device. In one embodiment, the device includes a separate module that communicates wirelessly with the implantable medical device and the separate module is user-removable from the portable device.

The present subject matter also includes a method and apparatus to allow a portable communicator, such as a PDA or cellular telephone, to interface between an implantable medical device and a programmer. The programmer may be coupled to the portable device by a network communication connection. For example, in one embodiment, a remote programmer can access a cellular telephone coupled to a portable device via the Internet, a private area branch exchange (PABX, also known as a PBX), an intranet network, an ethernet connection or other remote communication means. In one embodiment, the portable device is coupled to a portable telephone with which the programmer communicates using a public switched telephone network (PSTN) and the portable telephone is in wireless communication with the implantable medical device.

The present system may allow increased data logging, thereby permitting analysis otherwise not possible using the limited data storage capacity and battery capacity of an implanted device.

BRIEF DESCRIPTION OF THE FIGURES

FIGS. 1B, 1C, 1D, 1E illustrate screen shots appearing on a portable communicator according to one embodiment.

DETAILED DESCRIPTION

Figure 1A:
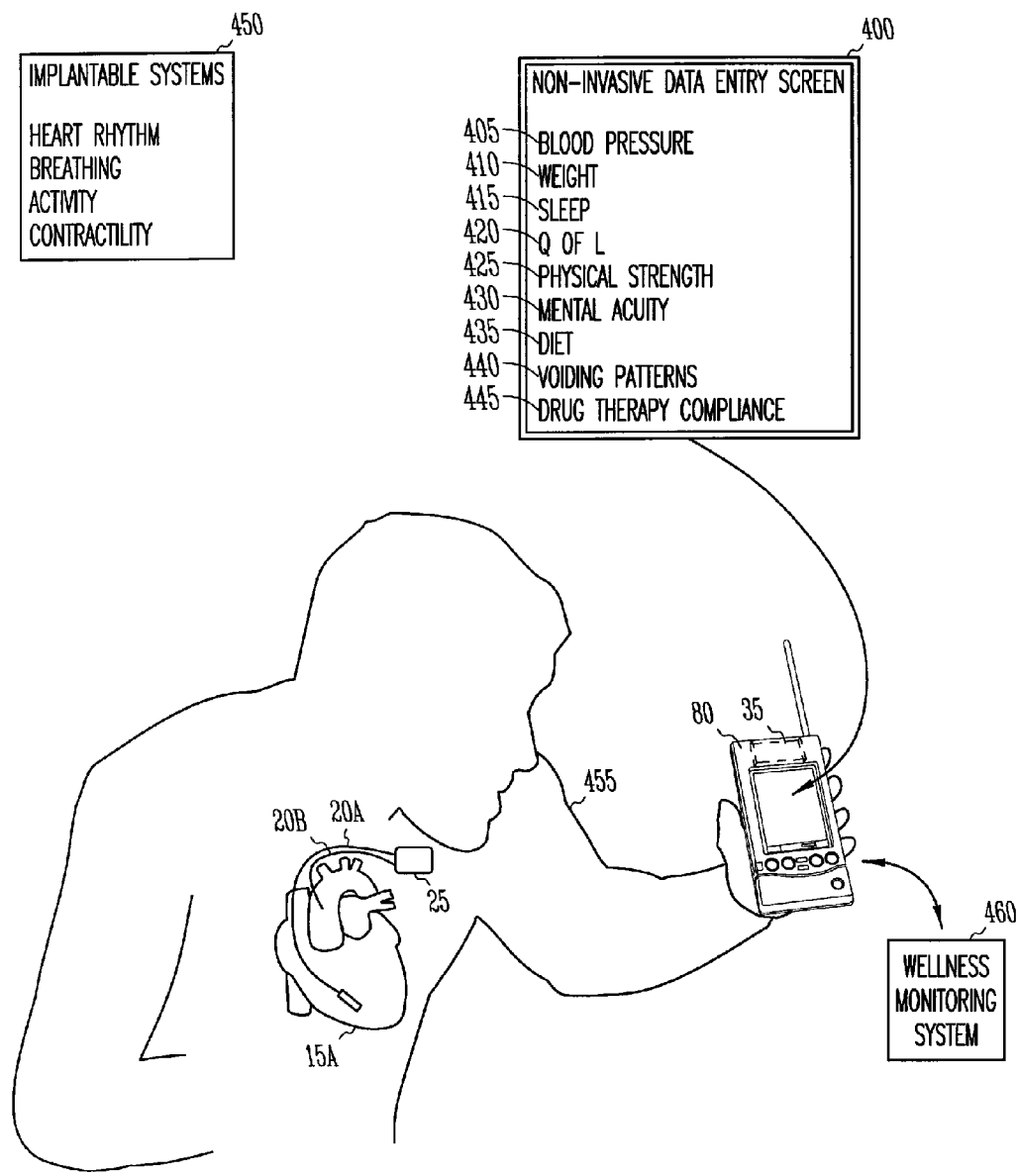
FIG. 1A illustrates a patient with an implanted medical device holding a portable communicator as well as a screen shot of the portable communicator.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components. As used herein, the term data includes both data and programming.

In accordance with the present system, FIG. 1A illustrates patient 455 implanted with implantable medical device 25 coupled to heart 15A by leads 20A and 20B. In one embodiment, the combination of leads 20A and 20B and device 25 provides cardiac rhythm management pulsing and also senses one or more physiological parameters of heart 15A. Implantable medical device 25 communicates wirelessly with portable device 35 shown in the left hand of patient 455. Portable device 35 is external to the body of patient 455 and, in the embodiment shown, is coupled to portable communicator 80. In one embodiment, portable communicator 80 includes a PDA.

In one embodiment, implantable medical device 25 provides data including heart rhythm, breathing, activity, and contractility, as illustrated at 450. Other types of data derived from implantable systems are also contemplated, as noted at 450. For example, in one embodiment, a respiration sensor is implanted into patient 455 and communicates with portable device 35. Data received from such implantable systems may be perceived as involuntary, or passive, data since the patient has no control over the process of collecting and transmitting the data from such sources.

In one embodiment, portable communicator 80 includes a touch-sensitive display screen for displaying information to a user or patient 455. Depending on the application executing on portable communicator 80, the display screen may provide prompts, messages, questions, or other data designed to elicit an input from patient 455. For example, in one embodiment, portable communicator 80 may display a screen shot as shown at 400. Screen shot 400, entitled "Non-invasive Data Entry Screen" provides links to questions or prompts as shown in the figure. Data received from such interactive prompts may be perceived as voluntary, or active, data since the cooperation and active input of the patient is part of the data collection process. The user voluntarily provides answers in response to prompts that appear on the screen. At each of 405 through 445, the patient may be linked to one or more questions concerning the general topic appearing in screen shot 400. For example, at 405, the link "Blood Pressure" may lead to one or more questions concerning the patient's blood pressure. At 410, the patient may be prompted for information concerning their body weight. At 415 the patient may be prompted to supply data concerning their sleep patterns (bedtime, sleep time, perceived arousals, perceived sleep quality) or recent life experiences. At 420, the patient may be prompted for data concerning their perceived quality of life (Q of L). At 425, the patient may be prompted to supply information concerning their perceived physical strength. At 430, the patient may be prompted to supply information regarding their mental acuity. In one embodiment, the patient may be presented with a series of short questions and based on the responses received, portable communicator 80 calculates a parameter corresponding to mental acuity. At 435, the patient is prompted for data concerning their dietary intake. At 440, the patient is prompted for data concerning their voiding patterns. At 445, the patient is prompted to supply information concerning drug therapy compliance.

Wellness monitoring system 460 is in communication with portable communicator 80, and thus, portable device 35. Wellness monitoring system 460 provides analysis of voluntary and involuntary data gathered by portable device 35. In one embodiment, wellness monitoring system 460 includes computer and programming that conducts data analysis and identifies trends that may improve patient health and medical care.

FIG. 1B illustrates a screen shot of questions that may be posed in one embodiment. Questions and prompts appearing on a display coupled to portable device 35 may concern objective or subjective matter. Questions and prompts illustrated in the figure, concern the topics of exercising, prescribed medications, non-prescription drug intake, alcohol consumption and recent sleep patterns, however it will be appreciated that those shown are exemplary only and that other questions or prompts may also be used. In one embodiment, prompts are used in lieu of questions. For example, a prompt concerning exercising may be presented as "Enter the number of minutes and intensity of walking on a treadmill" thus calling for the user to enter numbers and/or levels of intensity on an analog scale.

FIG. 1C illustrates a screen shot of questions concerning alertness, unusual sensations, chest pain, anxiety, and stress. As noted other questions or subject matter may be presented to the patient.

FIG. 1D illustrates a screen shot of questions directed to eating a balanced diet, lethargy, insomnia, voiding patterns, and drug and dietary supplement intake.

FIG. 1E illustrates a screen shot of questions directed to exercise plans, recent alcohol consumption, weight relative to a target body weight, signs of edema and breathing difficulty (such as unexpected shortness of breath).

Figure 1F:
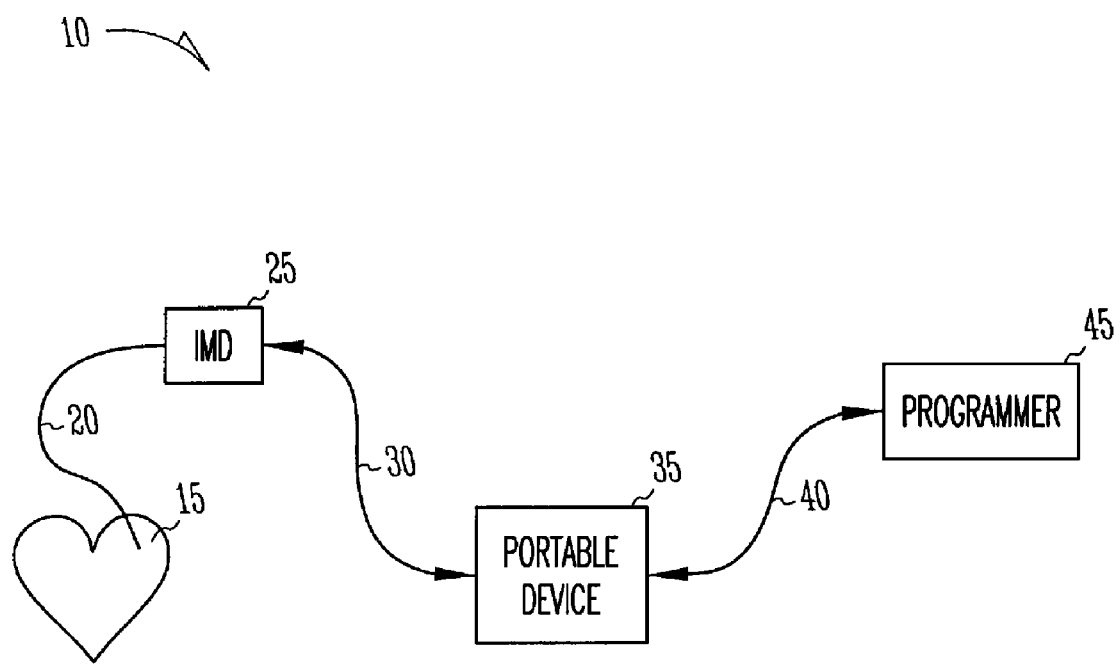
FIG. 1F illustrates a block diagram of an embodiment of the present system having a implantable medical device, a portable device, and a programmer.

FIG. 1F illustrates, in block diagram form, an embodiment of the present system. In the figure, system 10 is shown to include an implantable medical device, here marked IMD 25, which is shown coupled, by lead 20, to heart 15. In one embodiment, IMD 25 includes an implantable cardiac device (ICD), CRM device, pulse generator, or other implanted medical device that provides therapy to a patient or an organ of a patient, or that provides data derived from measurements internal to a patient. In the figure, IMD 25 is further shown coupled to portable device 35 by link 30. In one embodiment, portable device 35 includes a portable communicator. Portable device 35 is further coupled to programmer 45 by link 40.

In one embodiment, lead 20 includes a catheter or other implanted lead having one or more electrodes for the delivery of electrical energy to selected portions of an organ, or tissue, of a patient or for receiving electrical signals indicative of the health of the patient or a selected organ. In one embodiment, lead 20 is coupled to a human or animal heart, however, other organs may also be monitored or treated. In one embodiment, the housing of IMD 25 is electrically conductive and serves as an electrical conductor and operates in conjunction with a signal on a conductor portion of lead 20.

In one embodiment, IMD 25 includes a pacing device (commonly referred to as a pacemaker) a defibrillator, heart failure therapy device, cardiac resynchronization device or other medical device. In one embodiment, IMD 25 also includes circuitry and programming adapted to monitor the condition and performance of the pulse generator or other implanted device. For example, in one embodiment, IMD 25 provides data concerning the remaining battery condition for a power supply coupled to IMD 25. Such data may include information regarding remaining battery capacity or life, battery internal resistance or other measurable parameter. In other embodiments the data includes information regarding the electrical therapy provided by IMD 25. For example, in one embodiment, such data includes the peak voltage level, the rate, or frequency, of therapy, the profile of the delivered shock or other parameters. In various embodiments, IMD 25 is controlled by digital or analog signals and in one embodiment, IMD 25 generates data in digital or analog form.

In one embodiment, IMD 25 includes a program executing on an internal processor that controls the operation of the device. The program instructions reside in a memory accessible to the internal processor. By changing the program, or memory contents, the present system allows the operating program of IMD 25 to be dynamically tailored to a particular patient or condition. In one embodiment, the operating system, or memory contents of IMD 25 can be changed using wireless communication.

In one embodiment, IMD 25 includes a wireless transceiver. The transceiver operates using radio frequency transmissions, electromagnetic transmissions, magnetic coupling, inductive coupling, optical coupling, or other means of communicating without need of a wire connection between IMD 25 and another transceiver. In one embodiment, IMD 25 is coupled to a wireless transceiver by a wired connection.

In one embodiment, IMD 25 performs a data acquisition function. For example, a detector coupled to IMD 25 is adapted to monitor a fluid pressure, such as blood or urine. In one embodiment, the detector is adapted to monitor respiration, stress level, or other measurable biometric parameter. In one embodiment, monitoring includes determining an absolute or relative value for a particular biometric parameter. Internal memory within IMD 25 may be adapted to store a comparison value which may then be compared with a measured value thereby determining the performance of IMD 25 or the health of the patient.

Link 30 is a wireless communication link between IMD 25 and portable device 35. Link 30 allows communication in one or two directions. For example, in one embodiment, data from IMD 25 is communicated to portable device 35 with no data transmitted from portable device 35 to IMD 25. In this manner, portable device 35 functions as a data storage facility for IMD 25. In one embodiment, data stored in portable device 35 can be accessed by a treating physician and used for diagnosis, therapy or other purposes. Programming and controlling the operation of IMD 25 is performed using a programmer adapted to transmit commands, data or code to IMD 25. In one embodiment, portable device 35, or portable communicator 80, executes programming to analyze and process the data received from IMD 25. In one embodiment, communication link 30 may preclude transfer of data from portable device 35 to IMD 25 or to preclude transfer of data from IMD 25 to portable device 35. For example, in one embodiment, portable device 35 executes programming which automatically adjusts the performance or operation of IMD 25 independent of programmer 45 and under certain predetermined conditions, it may be desirable to preclude such automatic adjustments.

In one embodiment, data is communicated from portable device 35 to IMD 25 with no data transmitted from IMD 25 to portable device 35. In this manner, portable device 35 functions as an interface to communicate commands, data or code to IMD 25.

In one embodiment, data is communicated bidirectionally between IMD 25 and portable device 35. In various embodiments, link 30 entails a single bidirectional communication channel or includes multiple unidirectional communication channels which, when viewed as a whole, provide bidirectional communication. In one embodiment, a unidirectional communication channel operates using a particular frequency or communication protocol. For example, link 30 include a wireless radio frequency link compatible with a transmitter and receiver that uses frequency hopping, spread spectrum technology.

In one embodiment, internal memory within IMD 25 provides storage for data related to the CRM therapy provided to heart 15. The data may relate to the electrical, chemical or mechanical operation of the heart. In addition, IMD 25 includes memory for programming, comparison and other functions. In one embodiment, the contents of the memory regulates the operation of IMD 25.

In one embodiment, portable device 35 is coupled to a battery operated portable communicator having a processor, memory, and an output interface to communicate with a user and an input interface to receive user entered data. One suitable example of a portable communicator is that of a PDA. Commercial suppliers of PDAs include Palm, Inc. (Santa Clara, Calif.), Microsoft Corporation (Redmond, Wash.) and Handspring Inc., (Mountain View, Calif.) and others. Such devices typically include a display screen for presenting visual information to a user and a writing surface for entry of data using a stylus. Data may also be entered using a keyboard coupled to the portable communicator or by means of a wired or wireless communication link. Some portable communicator models also include an audio transducer, or sound generator, adapted to produce sounds that are audible by a user. In one embodiment, data from IMD 25 or programmer 45 is displayed on a screen coupled to portable device 35.

In one embodiment, portable device 35 is coupled to a portable telephone (such as a cellular telephone or a cordless telephone), a pager (one way or two way), or a computer (such as a handheld, palm-top, laptop, or notebook computer) or other such battery operated, processor based, portable communication device.

In one embodiment, portable device 35, or portable communicator 80, includes data storage and includes programming and instructions to conduct data processing. In one embodiment, the data storage capacity of portable device 35 or portable communicator 80 augments the data storage capacity of IMD 25, thus enabling a clinician to access a greater amount of contextual information regarding the medical condition of a user. For example, but not by way of limitation, the contextual information may assist in discovering and understanding relationships among different events.

In one embodiment, a wireless receiver is coupled to portable device 35 for purposes of receiving data from IMD 25. The wireless receiver may be internal or external to the housing of portable device 35. In one embodiment, a wireless transmitter is coupled to portable device 35 for purposes of transmitting data to IMD 25. The wireless transmitter may be internal or external to the housing of portable communicator 80. In one embodiment, a wireless transceiver is coupled to portable device 35 for purposes of both transmitting data to, and receiving data from, IMD 25. The wireless transceiver may be internal or external to the housing of portable device 35. In one embodiment, portable device 35 includes a telemetry head that is positioned near IMD 25 to facilitate wireless communications.

In one embodiment, circuitry or programming allows portable device 35 to trigger an alarm under predetermined conditions. For example, portable device 35 may sound an audible alarm or transmit an alarm signal if a biometric parameter exceeds a particular value or is outside a specified range of values. The alarm signal can be received by programmer 45 or a designated physician.

Referring again to FIG. 1F, link 40 is shown to couple portable device 35 with programmer 45. In one embodiment, link 40 includes a wired or wireless link that allows data communication between portable device 35 and programmer 45. In one embodiment, data is exchanged between portable device 35 and programmer 45 by means of a removable storage media.

In one embodiment, programmer 45 includes a processor based apparatus executing programming to communicate with IMD 25, portable device 35, or both. Typically, a clinician or physician will operate programmer 45 to communicate with IMD 25 using portable device 35 as a data interface. In particular, one embodiment provides that data from IMD 25 can be retrieved by accessing the memory of portable device 35. In one embodiment, programmer 45 transmits data to IMD 25 via portable device 35.

Figure 2:
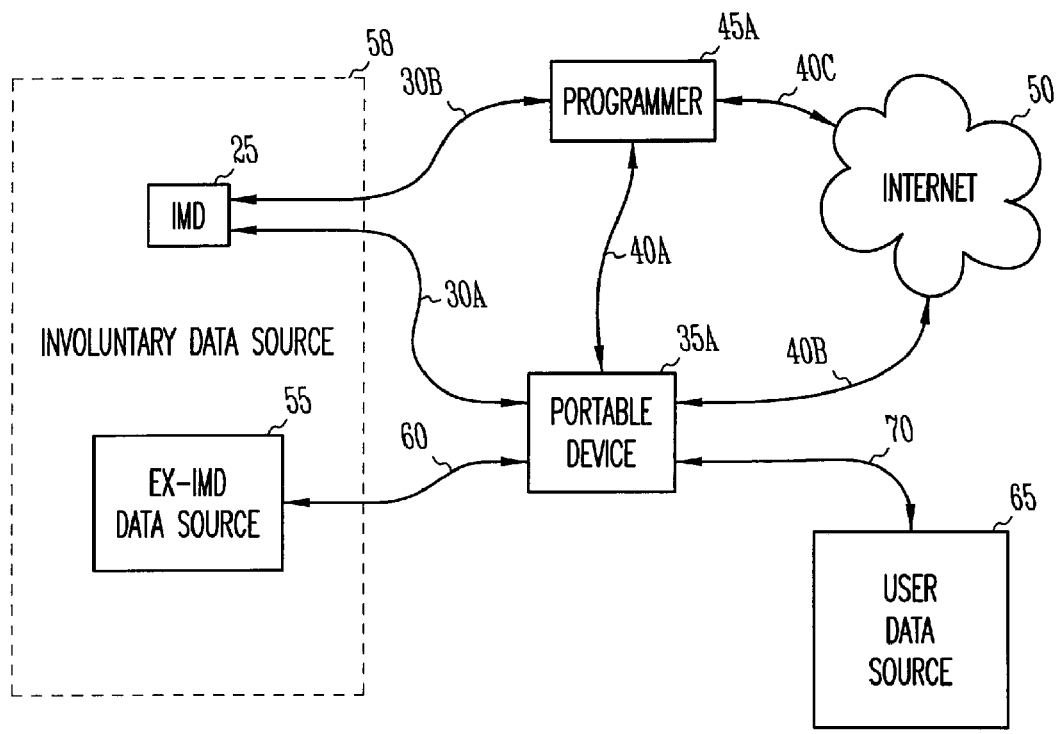
FIG. 2 illustrates a block diagram illustrating communication channels between involuntary data sources, a portable device, a programmer, a network, and a user data source.

FIG. 2 illustrates, in block diagram form, an embodiment of present system 10A. In the figure, IMD 25A is coupled to programmer 45A by wireless link 30B and to portable device 35A by wireless link 30A. Programmer 45A is further coupled to portable device 35A by link 40A and to network 50 by link 40C. Portable device 35A is further coupled to network 50 by link 40B. Portable device 35A receives data from involuntary data source 58 and exchanges data with user data source 65. Link 30A, link 30B, link 40A, link 40B, link 40C, and link 70 bear arrowheads on each end, and thus, are illustrated as bidirectional communication links. Nevertheless, it will be appreciated that some or all of the bidirectional communication links may be unidirectional. Furthermore, it will be appreciated that not all of the elements appearing in FIG. 2 may be present in one embodiment of system 10A.

To the extent that IMD 25A, portable device 35A, programmer 45A, link 30A, and link 40A are described elsewhere in this document, the following discussion concerns the elements not earlier described.

IMD 25A is coupled to programmer 45A via wireless link 30B. In one embodiment, link 30B include a handheld wand that is placed in the vicinity of IMD 25A to allow communication of data. In the figure, link 30B is shown to include a bidirectional communication channel.

Portable device 35A is coupled to programmer 45A via network 50 by way of link 40B and link 40C. It will be appreciated that network 50 may include the Internet, a private intranet, a wide area network (WAN), a local area network (LAN), or other communication network. In one embodiment, programmer 45A accesses network 50 using an ethernet connection, a dial-up connection, a cable modem connection, a digital subscriber line (DSL) connection, or other wired or wireless network connection. In one embodiment, portable device 35A accesses network 50 using an ethernet connection, a dial-up connection, a cable modem connection, a digital subscriber line (DSL) connection, or other wired or wireless network connection.

Portable device 35A is coupled to a block modeled in the figure as involuntary data source 58. Involuntary data source 58, in one embodiment, includes IMD 25A and ex-IMD data source 55, either of which can provide data to enable system 10A to tailor therapy of IMD 25 in an efficient manner. As described above, IMD 25A may include sensors that provide information, ultimately, to programmer 45A. In addition, in one embodiment, ex-IMD data source 55 may include an externally worn sensor or an implanted device. In one embodiment, an implanted device includes a second implanted medical device adapted to monitor a body organ or function, such as a blood oxygen monitor. Also by way of example, one externally worn sensor include a non-invasive data source such as a temperature monitor, blood pressure monitor or respiration monitor. In one embodiment, ex-IMD data source 55 is non-user worn. For example, in one embodiment, data is provided by an ambient temperature monitor or atmospheric pressure monitor. In one embodiment, a plurality of ex-IMD data sources 55 are provided. Data sources other than those enumerated herein are also contemplated.

Data provided by ex-IMD data source 55 is coupled to portable device 35A by link 60. In one embodiment, link 60 includes a wired coupling and in another embodiment, a wireless coupling. In one embodiment, ex-IMD data source 55 is coupled to, and integrated with, portable device 35A.

The data provided by ex-IMD data source 55 is received by portable device 35A. In various embodiments, processing of the data is conducted by portable device 35A or programmer 45A. In one embodiment, the data is provided in real time, (either continuously or according to a predetermined schedule) or upon a change exceeding a predetermined amount, or upon request or inquiry from programmer 45A or portable device 35A.

Portable device 35A is coupled to a block modeled in the figure as user data source 65, by link 70. In one embodiment, user data source 65 provides data volunteered by the user and is integrated with portable device 35A. User data source 65 includes, in one embodiment, a display screen, an audio generator and an input device. In operation, portable device 35A displays a question or prompt directed to the user and the user is instructed to respond by providing a manual input. For example, in one embodiment, portable device 35A sounds a characteristic tone and display a question concerning the well-being of a user. The user, in response to the prompt, may use a stylus, keyboard, voice response, or other means to indicate a suitable answer to the question presented. The data received from the user prompt is then stored by portable device 35A. In one embodiment, processing of the data received from user data source 65 is done by portable device 35A or by programmer 45A. User data source 65 may generate a prompt according to a predetermined schedule, randomly, or based on data received from portable device 35A, IMD 25 or environmental data source 55. In one embodiment, data is entered by the user on the user's initiative.

In one embodiment, programmer 45A receives data from several data sources and communicated via any of several data communication channels. For example, programmer 45A may receive data from IMD 25A via link 30B or via portable device 35A by way of link 30A and link 40A. In addition, programmer 45A may receive data from IMD 25A via network 50 by way of link 30A, link 40B and link 40C. Data may be acquired using an interrupt driven system or on a query-based system.

In addition, one embodiment provides that data from IMD 25A is communicated to programmer 45A via any of several communication paths. For example, data may be communicated to programmer 45A using link 40A, 40B, 40C, 60 or 70.

Figure 3:
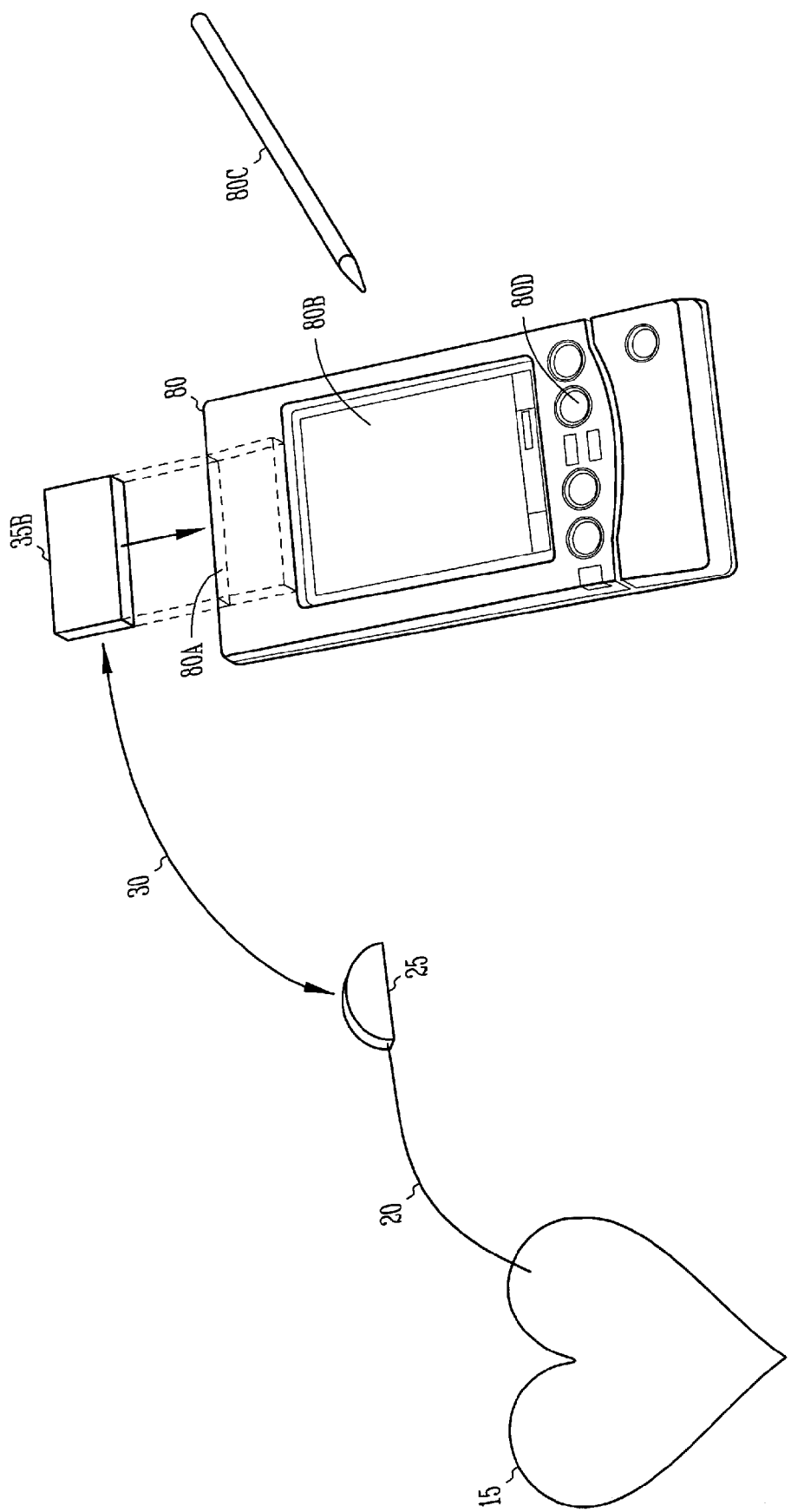
FIG. 3 illustrates a perspective view of a PDA with a removable portable device, in communication with an implantable cardiac device coupled to a heart.

FIG. 3 illustrates a perspective view of an embodiment of the present subject matter. In the figure, portable communicator 80 includes a display screen 80B, a plurality of user operable buttons 80D, and expansion port 80A. Expansion port 80A receives, and electrically couples to, portable device 35B. Stylus 80C may be used to manually enter data using screen 80B. Portable device 35B is wirelessly coupled to implanted device 25 which, in the embodiment shown, is further coupled by electrode 20 to heart 15.

Consider the operation of the embodiment in FIG. 3. Link 30 is illustrated as a bidirectional link and thus, data from device 25 is wirelessly telemetered to portable device 35B. In addition, data, or programming from portable device 35B is wirelessly telemetered to device 25. At various times, portable communicator 80 will generate a prompt calling for a response in the form of a user input. A user may enter data using any of a variety of means. For example, a response may be entered using stylus 80C, buttons 80D, or an external keyboard. In one embodiment, portable communicator 80 responds to voice commands received from a user. A prompt may be visually displayed using screen 80B or audibly generated using an internal sound generator. Manually entered data received from a user, as well as data received from other inputs (some of which were described relative to FIG. 2) is stored using portable communicator 80. The data stored in portable communicator 80 is then available for processing, and to tailor the therapy. Data may be processed by portable communicator 80, portable device 35, or by programmer 45, In addition to data entry, in one embodiment, stylus 80C, along with screen 80B, and buttons 80D, allow a user to exercise limited control over the operation of implantable medical device 25. In one embodiment, reasonable constraints on the authority to change the operation of device 25 are established and implemented by a clinician using programmer 45.

Figure 4:
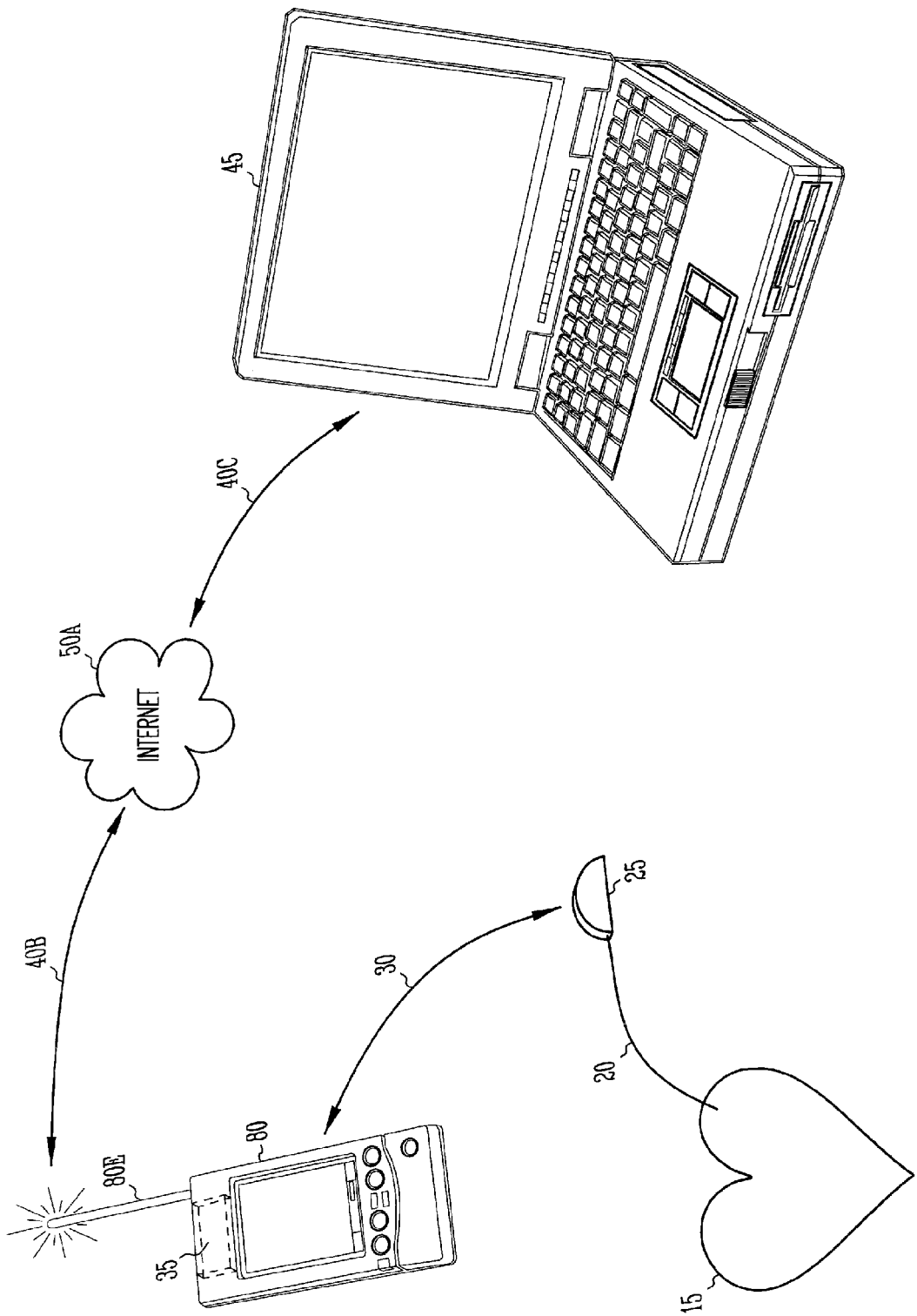
FIG. 4 illustrates a system according to the present subject matter including a PDA wirelessly coupled to an implantable cardiac device and wirelessly coupled to the Internet and further coupled to a remote programmer.

FIG. 4 illustrates a perspective view of an embodiment of the present subject matter. In the figure, portable communicator 80 includes wireless communication antenna 80E. Portable communicator 80, in this embodiment, is adapted for wireless Internet access to network 50A using link 40B. In one embodiment, link 40B includes a radio frequency communication link. In this embodiment, portable communicator 80 includes an internally mounted portable device 35.

Programmer 45 accesses Internet 50A via link 40C. In one embodiment, link 40C includes a dial-up modem connection, a cable modem connection, a DSL connection, an ISDN line, or other channel providing access to the Internet.

Using the system of FIG. 4, a user may compile contextual information regarding ICD 25, as well as himself, using portable communicator 80. In one embodiment, a clinician using programmer 45 may remotely access the data stored in portable communicator 80 using link 40C, Internet 50A and link 40B. In this manner, programmer 45 may wirelessly receive the data, process the data, and transmit data and code to change the future operation of device 25.

Figure 5:
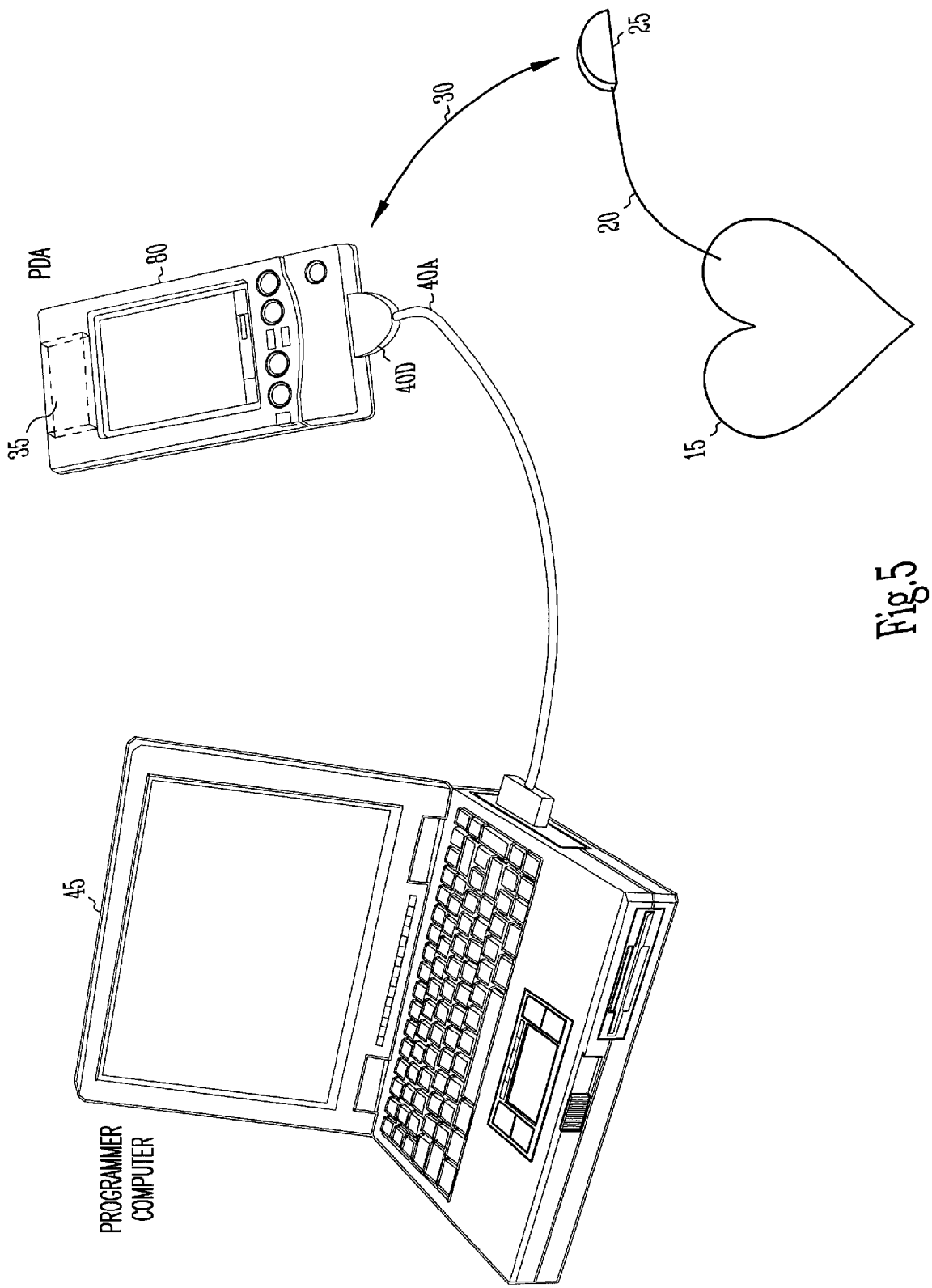
FIG. 5 illustrates a system according to the present subject matter including a PDA wirelessly coupled to an implantable cardiac device and coupled to a programmer via a wired connection.

FIG. 5 illustrates a perspective view of an embodiment of the present subject matter. In the figure, portable communicator 80 includes portable device 35 and is coupled to IMD 25, heart 15 and electrode 20, by wireless link 30. Portable communicator 80 is further coupled to programmer 45 by link 40A and connector 40D.

Using the system of FIG. 5, a clinician operating programmer 45 is able to exchange data or code with portable communicator 80 using link 40A. Connector 40D is a multi-conductor connector providing access to data of portable communicator 80. Portable device 35 is internal to portable communicator 80. It will be appreciated that link 40A may couple portable communicator 80 to a local area network or other communication network. For example, portable communicator 80 may be connected to a PSTN using link 40A, and thus, programmer 45 may exchange data with portable communicator 80 using a modem coupled to PSTN.

Figure 6A:
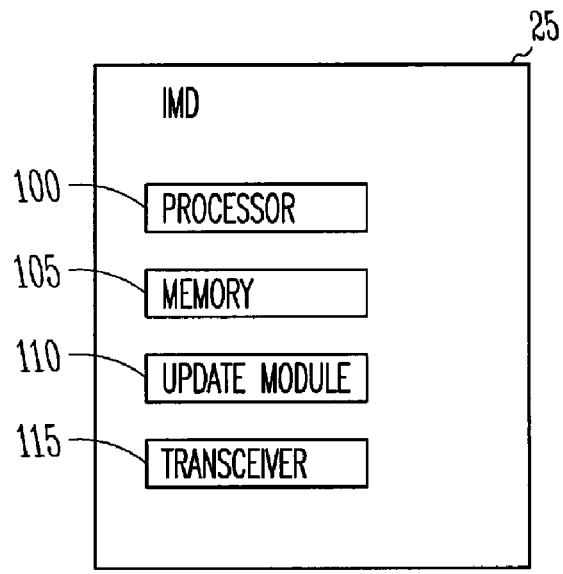
FIG. 6A illustrates a block diagram of an implantable medical device for one embodiment of the present system.

FIG. 6A illustrates a block diagram of an implanted medical device for one embodiment of the present system. In the figure, IMD 25 is shown to include processor 100, memory 105, update module 110 and transceiver 115. In operation, processor 100 governs the operation of IMD 25 and executes programming stored in memory 105. In addition to the executable program, memory 105 also includes data storage regarding the patient and IMD 25. Update module 110 operates in conjunction with processor 100, memory 105 and transceiver 115 to receive, install, and execute new instructions for execution by processor 100.

Figure 6B:
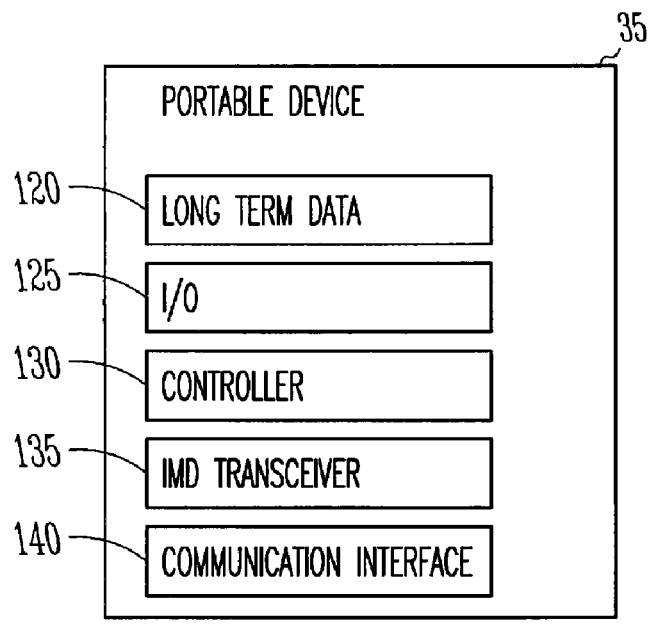
FIG. 6B illustrates a block diagram of a portable device for one embodiment of the present system.

FIG. 6B illustrates a block diagram of a portable device for one embodiment of the present system. In the figure portable device 35 is shown to include long term data storage 120, input/output 125, controller 130, IMD transceiver 135 and communication interface 140. Long term data storage 120 augments the data storage capacity of memory 105 of IMD 25. In one embodiment, storage 120 is of a greater capacity than that of memory 105. In addition, storage 120 may be of a physically larger size, be less expensive than medical grade implantable memory, and more robust.

Input/output 125, IMD transceiver 135 and communication interface 140, in conjunction with controller 130 enables receipt and transmission of data from IMD 25 as well as data from programmer 45. IMD transceiver 135 and transceiver 115 provide a wireless telemetric link between IMD 25 and portable device 35.

Portable device 35 may be coupled to a portable communicator and one or more of long term data 120, input/output 125, controller 130, IMD transceiver 135, or communication interface 140 may be provided by the portable communicator.

Figure 7:
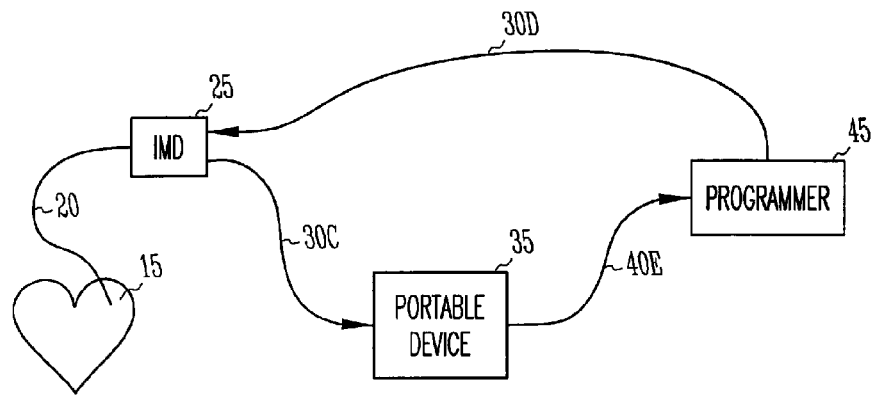
FIG. 7 illustrates one embodiment of the present subject matter having an implantable medical device communicating data to a portable device which, in turn, communicates with a programmer and the programmer is coupled to the implantable medical device.

FIG. 7 illustrates in block diagram, an embodiment of the present subject matter. In one embodiment, CRM therapy, for CHF is provided to heart 15 by IMD 25 via lead 20. Data accessible to IMD 25 is wirelessly communicated to portable device 35 via link 30C. Portable device 35 operates as a data storage facility for IMD 25 and in one embodiment, performs data processing.

Programmer 45 receives data from portable device 35 via link 40E. In one embodiment, programmer 45 performs data processing. Updated programming for execution by IMD 25 is determined by programmer 45 and transmitted wirelessly to IMD 25 via link 30D. Updated programming may be based on data received from portable device 35, as well as manual inputs received at programmer 45. IMD 25 includes a transmitter to communicate using link 30C and a receiver to communicate using link 30D.

In the embodiment illustrated in FIG. 7, portable device 35 provides a communication link for data communicated from IMD 25 to programmer 45. It will be understood that other data may also be received, processed and stored by portable device 35 as well as programmer 45. For example, a non-invasive data source may provide data to portable device 35.

Figure 8:
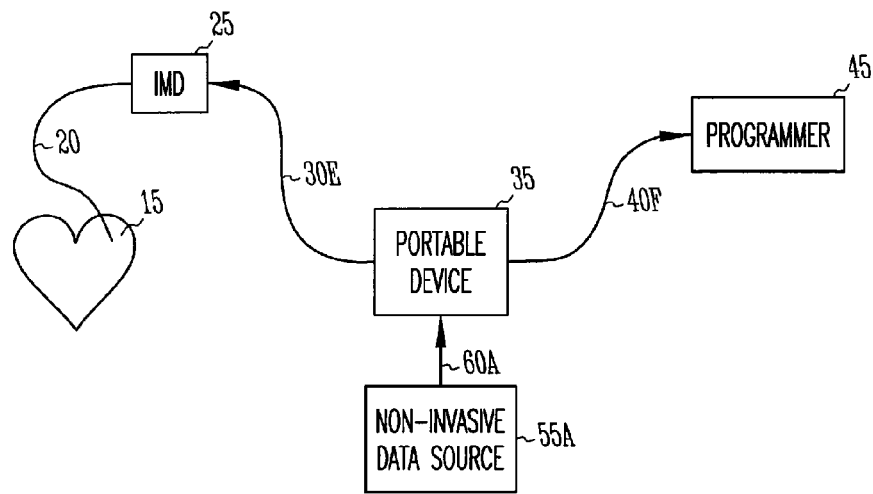
FIG. 8 illustrates one embodiment of the present system including an implantable medical device receiving data from a non-invasive data source provided to a portable device, and further communicating with a programmer.

FIG. 8 illustrates in block diagram, an embodiment of the present subject matter. In the figure, CRM therapy is provided to heart 15 by IMD 25 via lead 20. In the embodiment shown, IMD 25 includes a wireless receiver that receives transmissions from portable device 35 via link 30E. In addition, portable device 35 also receives data from non-invasive data source 55A via link 60A. Link 60A may include a wired or wireless link. Data accessible to portable device 35 is communicated to programmer 45 via link 40F. Link 40F may be a wired or wireless link. Portable device 35 operates as a data storage facility for non-invasive data source 55A and in one embodiment, performs data processing. In one embodiment, programmer 45 performs data processing. Updated programming for execution by IMD 25 is determined by programmer 45 and communicated to portable device 35 by link 40F. Updated programming is transmitted wirelessly to IMD 25 via link 30E. Updated programming may be based on data received from portable device 35, as well as manual inputs received at programmer 45. IMD 25 includes a receiver to communicate using link 30E.

In the embodiment illustrated in FIG. 8, portable device 35 provides a communication link for data communicated from programmer 45 to IMD 25. As illustrated, non-invasive data, or other environmental data, may also be received, processed and stored by portable device 35 as well as programmer 45.

Figure 9:
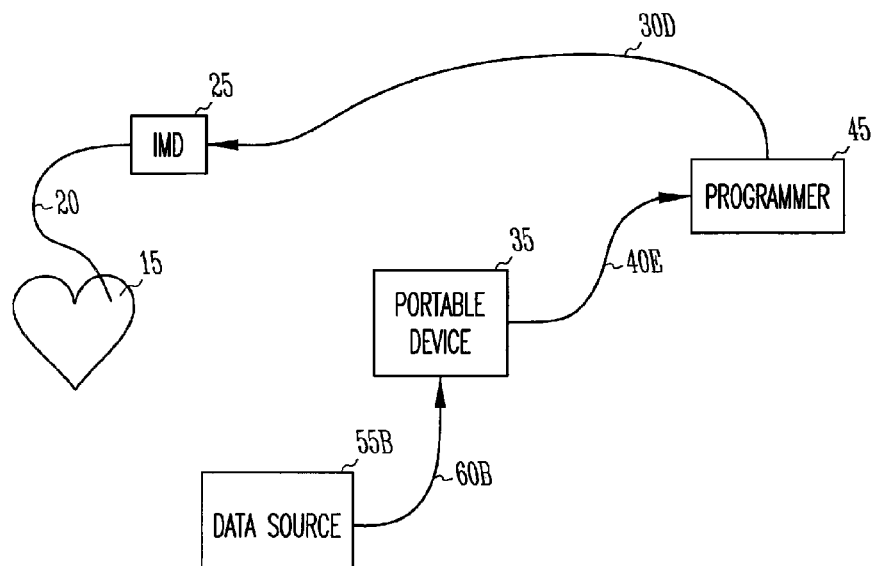
FIG. 9 illustrates one embodiment of the present system including a data source that provides data to a portable communicator which is coupled to a programmer which communicates with an implantable medical device.

FIG. 9 illustrates in block diagram, an embodiment of the present subject matter. In the figure, CRM therapy is provided to heart 15 by IMD 25 via lead 20. Data source 55B communicates with portable device 35 via link 60B. Portable device 35 operates as a data storage facility for data source 55B and in one embodiment, performs data processing. Programmer 45 receives data from portable device 35 via link 40E. In one embodiment, programmer 45 performs data processing. Data and updated programming for execution by IMD 25 is determined by programmer 45 and transmitted wirelessly to IMD 25 via link 30D. Updated programming may be based on data received from portable device 35, as well as manual inputs received at programmer 45. IMD 25 includes a wireless receiver to communicate using link 30D.

In the embodiment illustrated in FIG. 9, it will be understood that other data may also be received, processed and stored by portable device 35 as well as programmer 45. For example, a non-invasive data source or user entered data may provide data to portable device 35.

Figure 10:
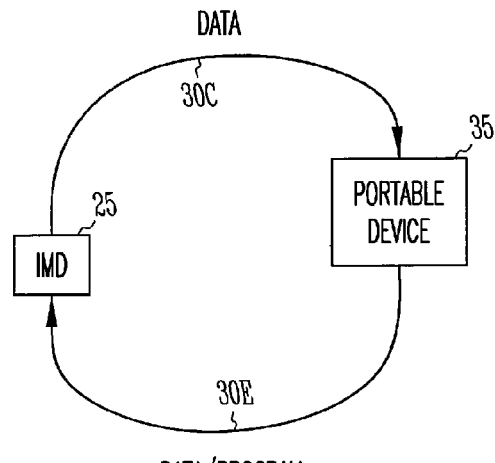
FIG. 10 illustrates, in block diagram, communication paths between an implantable medical device and a portable device.

FIG. 10 illustrates a portion of an embodiment of the present subject matter. In the figure, IMD 25 is in wireless communication with portable device 35. Arrow 30C illustrates the direction of data communication from IMD 25 to portable device 35. In one embodiment, data from IMD 25 includes, but is not limited to, operational data concerning the performance of IMD 25, diagnostic data concerning either IMD 25 or the patient, as well as patient medical information. Arrow 30E illustrates the direction of data and program information from portable device 35 to IMD 25. In one embodiment, data and program information from portable device 35 includes, but is not limited to, updated operating code, operational parameters, instructions, and executable code.

Figure 11:
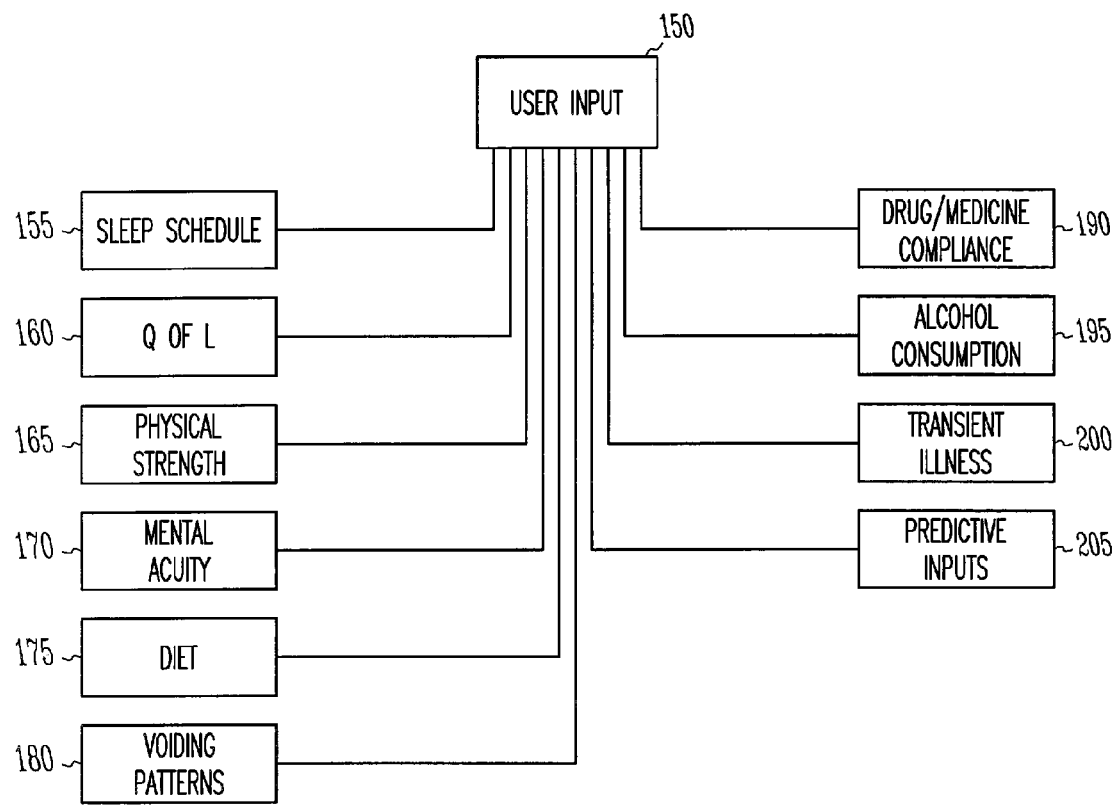
FIG. 11 illustrates selected types of user input data.

FIG. 11 illustrates, in block diagram form, user input data implemented in one embodiment of the present system. It will be appreciated that more or less than the illustrated data may be implemented in an embodiment. The user input data may be received from a user based on a prompt provided to the user, on an ad hoc basis as determined by the user, or as determined by a processor of the present system. The user may enter data using a menu based system, a graphical user interface (GUI), textual data or numerical data. FIG. 2 illustrates an embodiment of the present system having user data source 65 providing user input data.

At 155, the input data includes a sleep schedule. The sleep schedule may describe the sleep (or wake) times of the user. The user may enter the data into portable device 35. In an embodiment including portable device 35 coupled to portable communicator 80, the data may be entered, for example, using stylus 80C, keys 80D or a keyboard. At 160, the input data includes a user-selected quality of life index. The user may select and specify a suitable response based on subjective or objective criteria. At 165, the input data includes an entry corresponding to the user's physical strength. At 170, the input data includes an entry corresponding to the mental acuity of the user. In this instance, portable communicator 80 may determine a value based on predetermined criteria which may entail analysis of a series of user entered responses. At 175, the input data includes information concerning the recent dietary intake of the user. Data may include caloric content, nutritional content (sodium levels), quantity and type of foods. At 180, the input data may include user provided data concerning voiding patterns or behavior. At 190, the input data may include drug intake or medicine compliance information. At 195, the input data may include alcohol consumption information such as quantity, type and time of intake. At 200, the input data may include transient illness information concerning such matters as time of onset, symptoms, treatment and recovery. At 205, the input data may include miscellaneous predictive input information. For example, the user may enter data to indicate that he will soon be walking or running or otherwise exercising. Other input data may also be provided depending upon the circumstances of the patient. The user input information may be tailored by the treating physician using programmer 45 and portable device 35. For example, the data collection protocol may be tailored to reduce battery consumption by prompting the user for a response at a reduced frequency.

Figure 12:
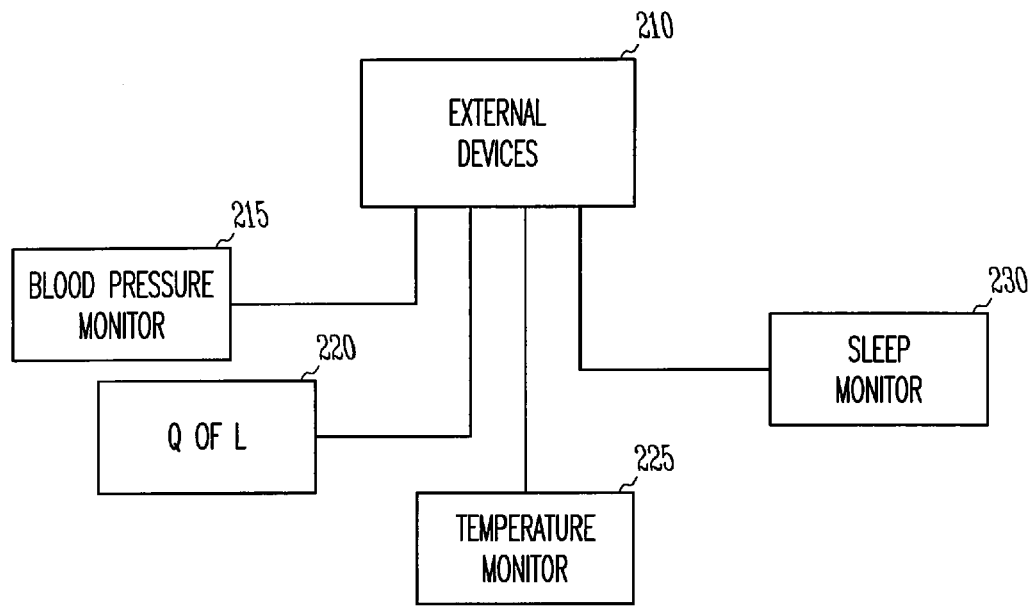
FIG. 12 illustrates selected types of external devices.

FIG. 12 illustrates, in block diagram form, a selection of external, or non-invasive, devices 210 that may be implemented in one embodiment of the present system. It will be appreciated that more or less than the illustrated devices may be implemented in an embodiment. External devices 210 provide environmental data that may be received by portable device 35 of the present system. Data may be generated by external devices 210 and provided, in digital form, to portable device 35 by a wired or wireless link. FIG. 2 illustrates an embodiment of the present system having environmental data source 55 including external device data sources.

At 215, the external device includes a blood pressure monitor. Encoded blood pressure information for the patient is provided as a function of time or other measured parameter. At 220, the external device includes an objective measure of the patient's quality of life. In one embodiment, this may entail a sensor adapted to correlate with quality of life. At 225, the external device includes a temperature monitor. Encoded temperature information is provided as a function of time or other measured parameter. The measured temperature may correspond to a body temperature, an ambient temperature, or other temperature. At 230, an external device provides data concerning the sleep time of the patient. The device may include a monitor coupled to a clock or a monitor coupled to another device corresponding to sleep time and sleep phase variation.

Figure 13:
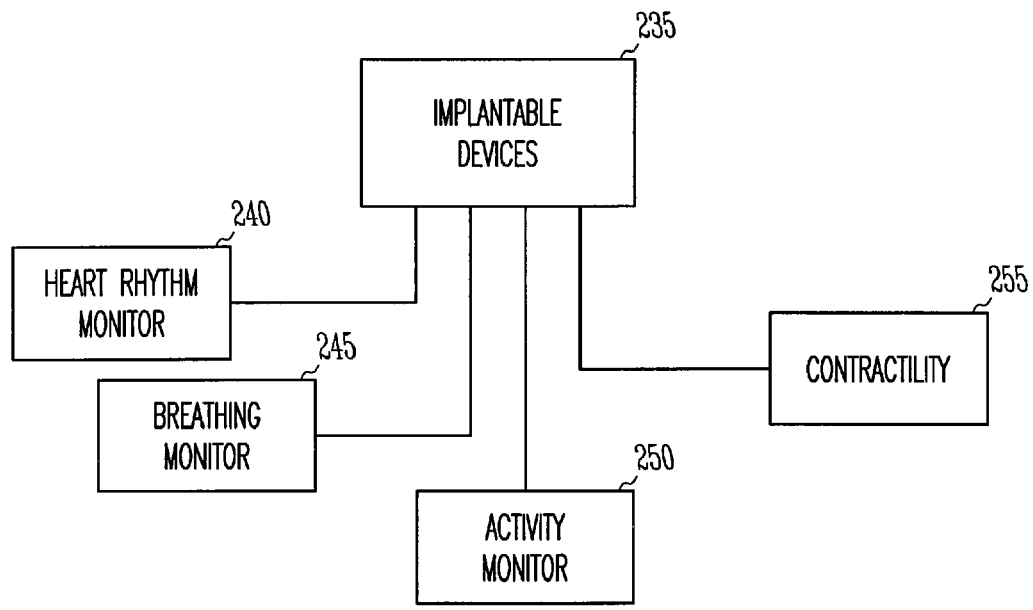
FIG. 13 illustrates selected types of implantable devices.

FIG. 13 illustrates, in block diagram form, a selection of implantable devices 235 that may be implemented in one embodiment of the present system. It will be appreciated that more or less than the illustrated devices may be implemented in an embodiment. Implantable devices 235 provide internal data that may be received by portable device 35 of the present system. Such data may be generated and provided, in digital form, to portable device 35 by a wired or wireless link. The implantable devices each provide a signal that is encoded and wirelessly communicated to portable device 35. FIG. 2 illustrates an embodiment of the present system having environmental data source 55 including implantable devices providing data.

At 240, the implantable device includes a heart rhythm monitor. At 245, the implantable device includes a respiration monitor. At 250, the implantable device includes an activity monitor. At 255, the implantable device includes a contractility measurement device.

Figure 14:
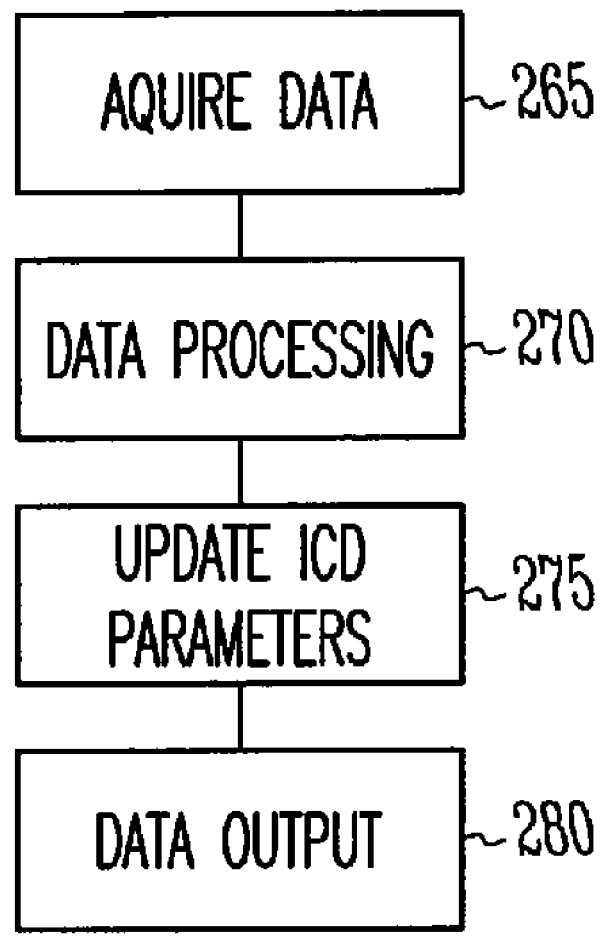
FIG. 14 illustrates an algorithm executed by one embodiment of the present subject matter.

FIG. 14 illustrates a method for analysis of trends using one embodiment of the present system. In one embodiment, method 260 is implemented by software or hardware using portable device 35 or other elements of system 10. At 265, data is acquired from various sources. Referring to FIG. 2, data may be acquired from IMD 25, programmer 45, network 50, environmental data source 55 and user data source 65. At 270, the acquired data is processed according to a procedure implemented in software. The procedure entails analysis of the data as a function of time or other measured parameter. At 275, the results of the data analysis are used to select an updated program or specify updated operational parameters for IMD 25. At 280, the updated program or operational parameters are transferred and implemented by IMD 25.

In one embodiment, a security protocol is implemented. The security protocol may assure authorized access for communications between programmer 45 and the portable device 35. In addition, one embodiment provides secure communications between portable device 35 and IMD 25. Authorization may be limited to reading data or reading and editing data. Security may entail a password and username system, encryption, or other biometric authentication system to prevent unauthorized access.

The present system provides data that may be useful in trend analysis, and thus, improve health care for a patient. For example, the present system may allow monitoring of device performance over an extended duration. Long term device performance data may facilitate improved therapy. In addition, the present system may allow cost-effective compilation of patient medical data. Such historical data may prove beneficial in developing treatment protocols for the patient.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

We claim:

1. A system capable of dynamically tailoring performance of an implantable medical device, the system comprising:
    an implantable wireless transmitter coupled to the implantable medical device;
    a portable wireless receiver in communication with the implantable wireless transmitter; and
    a portable communicator coupled to the portable wireless receiver and configured to execute a set of instructions to present a query, receive a user response to the query and receive data from the implantable wireless transmitter and correlate the user response with the received data to form correlated data;
    a programmer in communication with the portable communicator and configured to dynamically tailor performance of the implanted medical device based on the correlated data.

2. The system of claim 1 wherein the portable communicator includes a display configured to present a health question to a user.

3. The system of claim 1 further comprising an external sensor in communication with the portable communicator.

4. The system of claim 3 wherein the external sensor includes at least one of a physiological sensor and an environmental sensor.

5. The system of claim 1 further comprising an implantable wireless receiver coupled to the implantable medical device and further comprising a portable wireless transmitter in communication with the portable communicator.

6. The system of claim 1, wherein the correlated data further comprises sensor data from a sensor data source, and wherein the sensor data source is configured to communicate with the portable communicator.

7. The system of claim 1 further comprising a wireless coupling between the programmer and the portable communicator.

8. The system of claim 1 further comprising a set of instructions for execution by the portable communicator to communicate data from the portable communicator to the programmer.

9. The system of claim 1 wherein the implantable medical device includes at least one of a cardiac pacing device, a heart failure therapy device, a cardiac resynchronization device, and a defibrillator device.

10. The system of claim 1 further comprising a set of instructions for execution by the portable communicator to cause the portable communicator to alert a user when predetermined data is received by the portable communicator.

11. An apparatus capable of dynamically tailoring performance of an implantable medical device, the apparatus comprising:
    a portable communicator;
    a receiver coupled to the portable communicator and configured for wireless communication with the implanted medical device; and
    a set of instructions executable by the portable communicator and adapted to cause the portable communicator to store telemetered data received from the implanted medical device and contextual data received by the portable communicator and to correlate the telemetered data and contextual data to form correlated data;
    a programmer in communication with the portable communicator and configured to dynamically tailor performance of the implanted medical device based on the correlated data.

12. The apparatus of claim 11 further including an interface coupled to the portable communicator and enabling communication of data between the portable communicator and a programmer.

13. The apparatus of claim 12 wherein the interface is configured to communicate with the programmer by a wireless coupling.

14. The apparatus of claim 11 wherein the receiver is configured to receive sensor data from at least one data source and wherein the set of instructions are adapted to cause the portable communicator to correlate the sensor data with the telemetered data and the contextual data to form correlated data.

15. The apparatus of claim 11 further including a transmitter coupled to the portable communicator and wherein the set of instructions are adapted to cause the transmitter to wirelessly communicate a signal to the implanted medical device to update programming of the implanted medical device.

16. A method of dynamically tailoring performance of an implantable medical device executable at one or more processors, the method comprising the acts of:
    using a transceiver module of a portable communicator to receive device data from the implantable medical device; and
    executing a program on a processor of the portable communicator, wherein the program includes instructions for storing the device data and storing contextual data received by the portable communicator from a user interface and correlating the device data and contextual data to form correlated data and communicating the correlated data with a programmer;
    wherein the programmer determines a dynamically tailored set of instructions based on the correlated data and transmits the set of instructions to the implantable medical device.

17. The method of claim 16 further comprising the act of using the transceiver module to receive device data from an external sensor.

18. The method of claim 16 further comprising the act of prompting a user to enter contextual data.

19. The method of claim 16 wherein the transmitted set of instructions controls the implantable device.

20. The method of claim 19 further comprising the act of receiving the instruction from the programmer.

21. A method of dynamically tailoring the performance of an implantable medical device executable at one or more processors, the method comprising the acts of:

receiving data from an implantable device using a portable communicator, the portable communicator configured for wireless communication with the implantable device and for communication with a programmer;

receiving a user input at the portable communicator;

correlating the data with the user input to form contextual information;

receiving the contextual information at the programmer;

generating updated programming based on the contextual information, the updated programming for execution by a processor at the implantable device; and transferring the updated programming to the implantable device.

22. The method of claim 21 wherein the act of generating updated programming includes receiving a manual input at the programmer.

23. The method of claim 21 wherein the act of receiving the contextual information at the programmer includes receiving a wireless signal.

24. The method of claim 21 wherein the act of transferring the updated programming is performed through use of a digital network.

* * * * *